United States Patent [19]

Atsumi et al.

[11] 3,953,441
[45] Apr. 27, 1976

[54] PREPARATION OF 2-BENZOYLALKYLBENZOMORPHAN

[75] Inventors: Toshio Atsumi; Kenji Kobayashi; Yoshiaki Takebayashi, all of Takarazuka; Hisao Yamamoto, Nishinomiya, all of Japan

[73] Assignee: Sumitomo Chemical Company, Limited, Osaka, Japan

[22] Filed: June 7, 1971

[21] Appl. No.: 150,841

[30] Foreign Application Priority Data
June 10, 1970 Japan............................ 45-50665
June 10, 1970 Japan............................ 45-50666
June 30, 1970 Japan............................ 45-57649

[52] U.S. Cl.................. 260/293.54; 260/297 R; 260/DIG. 13
[51] Int. Cl.² ................................ C07D 221/26
[58] Field of Search........... 260/293.54, DIG. 13, 260/297 R

[56] References Cited
UNITED STATES PATENTS

| | | | |
|---|---|---|---|
| 2,959,594 | 11/1960 | Gordon et al............... | 260/294.3 |
| 3,558,638 | 1/1971 | Clarke et al............... | 260/294.3 |
| 3,631,051 | 12/1971 | Atsumi et al.............. | 260/293.54 |
| 3,639,407 | 2/1972 | Clarke et al.............. | 260/293.54 |
| 3,644,373 | 2/1972 | Kigasawa et al........... | 260/293.54 |

*Primary Examiner*—G. Thomas Todd
*Attorney, Agent, or Firm*—Stevens, Davis, Miller & Mosher

[57] ABSTRACT

A novel process for preparing 2-benzoylalkylbenzomorphan derivatives and salts thereof, represented by the formula

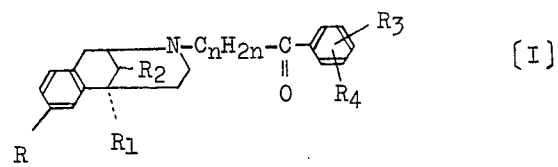

wherein $n$, R, $R_1$, $R_2$, $R_3$ and $R_4$ are as defined in the specification. The process comprises reacting a pyridinium derivative of the formula,

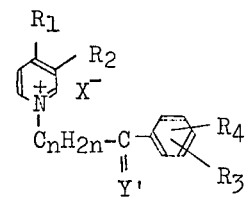

wherein X is a halogen atom and Y' is an ethylenedioxy group; with a Grignard reagent of the formula,

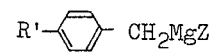

wherein R' is a hydrogen atom or a $C_1$–$C_3$ alkoxy group and Z is a halogen atom, to yield a 1,2-dihydropyridine derivative of the formula;

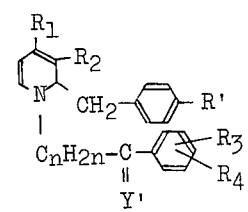

and then reducing the said 1,2-dihydropyridine derivative to give a 1,2,5,6-tetrahydropyridine derivative of the formula,

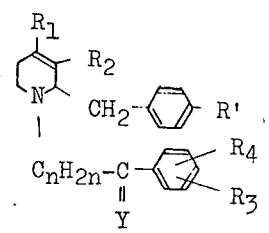

[I]

wherein Y is an oxygen atom or an ethylenedioxy group, and further cyclizing the obtained 1,2,5,6-tetrahydropyridine derivative.

9 Claims, No Drawings

PREPARATION OF 2-BENZOYLALKYLBENZOMORPHAN

This invention relates to a novel process for producing 2-benzoylalkylbenzomorphan derivatives and their salts which are useful as non-addicted analgesics and pain-relieving agents with calming effects.

More particularly, the invention pertains to a novel process for preparing 2-benzoylalkylbenzomorphan derivatives, and salts thereof, represented by the general formula,

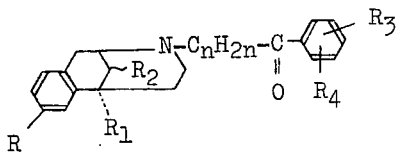  (I)

wherein R is a hydrogen atom, a hydroxyl group, a $C_1$–$C_3$ alkoxy group or an alkanoyloxy group; $R_1$ is a hydrogen atom, a $C_1$–$C_3$ alkyl group, a phenyl group, a halophenyl group, a $C_1$–$C_3$ alkylphenyl group, a $C_1$–$C_3$ alkoxyphenyl group, a hydroxyphenyl group, a trifluoromethylphenyl group, a nitrophenyl group, an aminophenyl group, a $C_1$–$C_3$ alkanoyloxyphenyl group or an alkanoyloxyphenyl group; $R_2$ is a hydrogen atom or a $C_1$–$C_3$ alkyl group; $R_3$ is a hydrogen atom, a halogen atom, a $C_1$–$C_3$ alkyl group, a $C_1$–$C_3$ alkoxy group, a $C_1$–$C_3$ alkylthio group, a nitro group, a trifluoromethyl group, an amino group or a hydroxyl group; $R_4$ is a hydrogen atom, a $C_1$–$C_3$ alkoxy group, a halogen atom or a $C_1$–$C_3$ alkyl group; and n is an integer of 2 to 4.

According to the present invention, the 2-substituted 6,7-benzomorphan derivatives (I) can be prepared by treating with a cyclizing agent 1-substituted 1,2,5,6-tetrahydropyridine derivatives, or salts thereof, represented by the general formula,

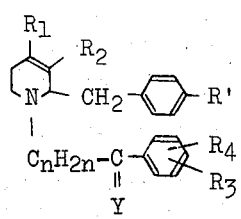  (II)

wherein $R_1$, $R_2$, $R_3$, $R_4$ and n are as defined above, Y is an oxygen atom or an ethylenedioxy group, R' is a hydrogen atom or a $C_1$–$C_3$ alkoxy group.

A few processes for producing these 6,7-benzomorphan derivatives have heretofore been described. For instance, it is known to obtain the 2-substituted 6,7-benzomorphan derivative and then demethylating the compound with cyanogen bromide, and substituting the obtained 2-unsubstituted 6,7-benzomorphan derivative. E. L. May, Journal of Organic Chemistry, 24, 1435, (1959) This process is shown, for example, as follows:

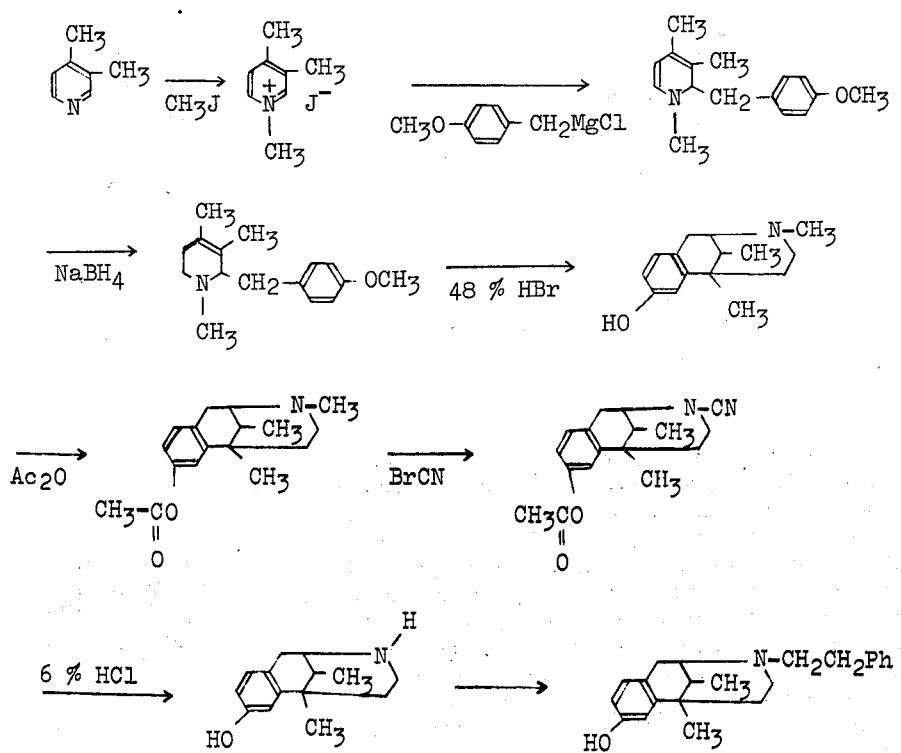

In our specification of Belgian Pat. Publication No. 743,733/1969, there is described a process which is represented by the following scheme;

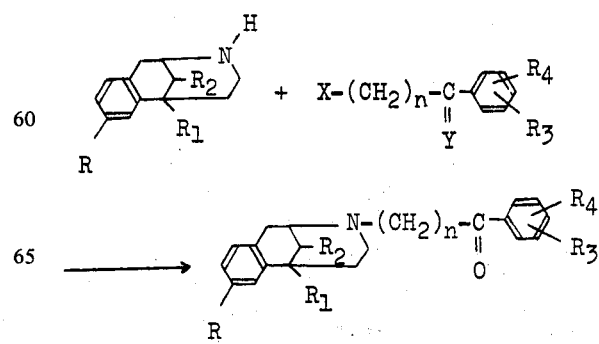

wherein R is a hydrogen atom, a hydroxyl group or $C_1-C_3$ alkoxy group; $R_1$ and $R_2$ are a $C_1-C_3$ alkyl group; $R_3$ is a hydrogen atom, a halogen atom, a $C_1-C_3$ alkoxy group, a $C_1-C_3$ alkyl group, a $C_1-C_3$ alkylthio group, a nitro group, a trifluoromethyl group, an amino group or a hydroxyl group; $R_4$ is a hydrogen atom, a $C_1-C_3$ alkoxy group, a $C_1-C_3$ alkyl group or a halogen atom.

Thus, these processes are very complicated and the yield of the desired product is very poor.

Contrary to these procedures, the present invention can be represented by the following reaction scheme:

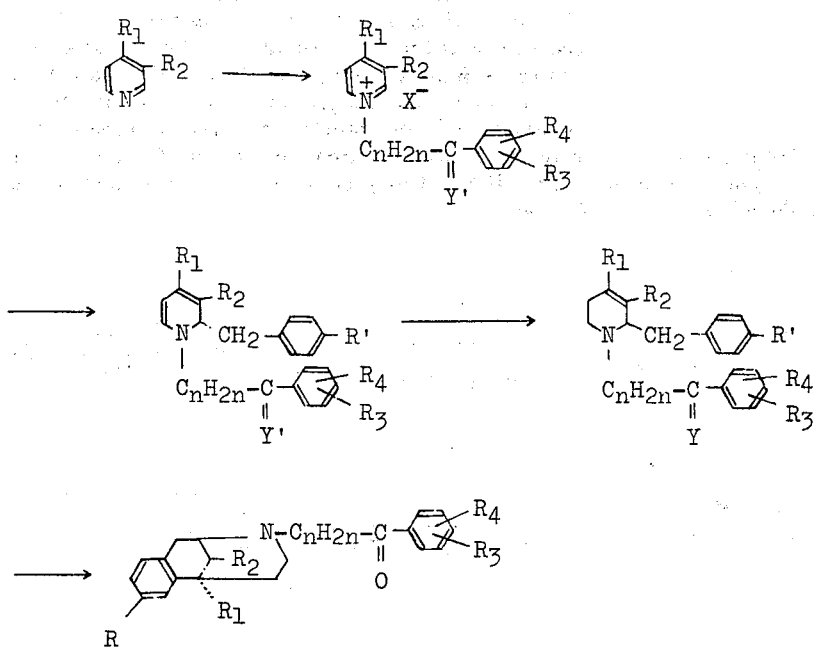

wherein R', $R_1$, $R_2$, $R_3$, $R_4$, Y and n are as defined above; Y' is an ethylenedioxy group; and X is a halogen atom. As shown in the above reaction scheme, the present invention has only four processes to produce the 6,7-benzomorphan derivative of the formula [I], and further we have found that 6,7-benzomorphan derivative of the formula [I] can be smoothly and economically prepared in high yield. Thus, this new and useful process is superior markedly to the known methods and represents an improvement thereover.

The 1-substituted 1,2,5,6-tetrahydropyridine derivatives of the formula [II] are novel compounds. They are easily prepared by reducing novel 1-substituted 1,2-dihydropyridine derivatives of the formula,

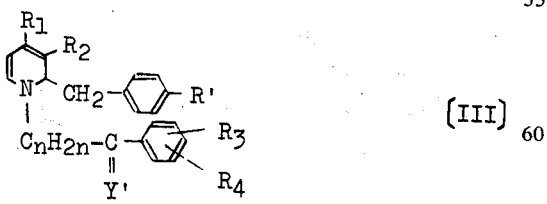

(III)

wherein R', $R_1$, $R_2$, $R_3$, $R_4$, Y' and n are defined above.

The novel 1,2-dihydropyridine derivatives of the formula [III] can be prepared by reacting a pyridinium derivative of the formula,

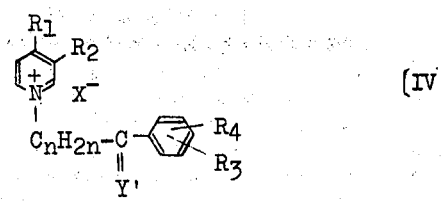

(IV)

wherein X, $R_1$, $R_2$, $R_3$, $R_4$, Y' and n are as defined above, with a Grignard reagent represented by the formula,

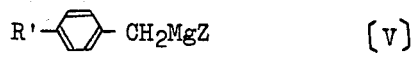

(V)

wherein Z is a halogen atom and R' is as defined above.

Further, the compounds of the formula [IV] are also novel compounds, which are prepared by reacting the corresponding pyridine derivatives of the formula,

(VI)

wherein $R_1$ and $R_2$ are as defined above, with an alkyl halide derivative of the formula

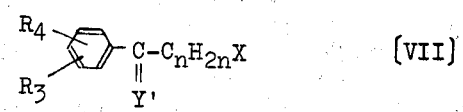

(VII)

wherein X, Y', n, $R_3$ and $R_4$ are as defined above.

In accordance with the present invention, the method for producing the 2-substituted 6,7-benzomorphan derivatives of the formula [I] may be represented, in general, by the following reaction scheme:

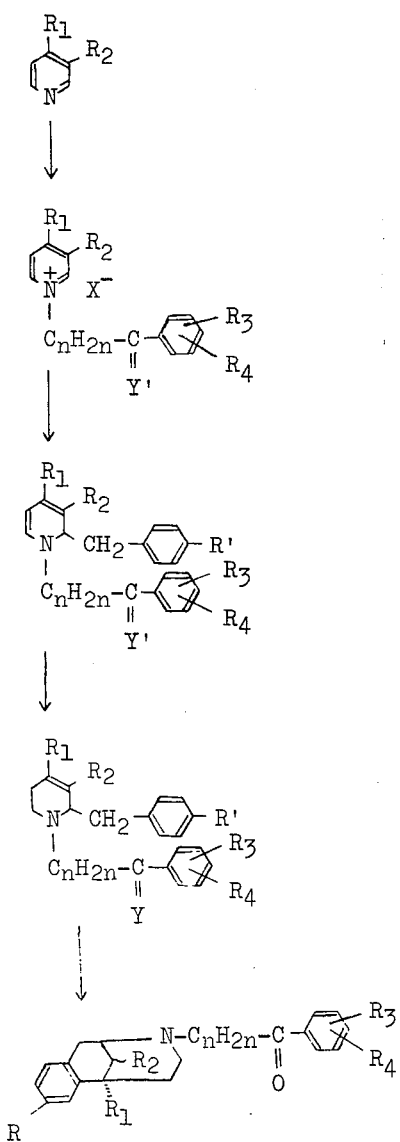

An object of the present invention is to provide a novel process for preparing 2-substituted 6,7-benzomorphan derivatives and salts thereof, in high yield and in high purity.

Another object is to provide a novel process for preparing salts of 2-substituted 6,7-benzomorphan derivatives of the formula [I].

A further object is to provide a process for preparing novel pyridine derivatives.

Other objects of the invention will become apparent from the description that follows.

In order to achieve the above objects, the present invention provides a process for preparing 2-substituted 6,7-benzomorphan derivatives represented by the formula [I], which comprises reacting a 1-substituted 1,2,5,6-tetrahydropyridine derivative represented by the formula [II], or a salt thereof, with a cyclizing agent.

Further, the present invention provides a process for producing salts of 6,7-benzomorphan derivatives of the formula [I], which comprising reacting a 1-substituted 1,2,5,6-tetrahydropyridine derivative of the formula [II], or a salt thereof, with a suitable cyclizing agent to yield the 2-substituted 6,7-benzomorphan derivative of the formula [I], and then reacting the said 2-substituted 6,7-benzomorphan derivative with an inorganic acid or an organic acid.

According to this invention, 2-substituted 6,7-benzomorphan derivatives are prepared from 1-substituted 1,2,5,6-tetrahydropyridine derivatives represented by the formula [II], or salts thereof, by cyclizing with the Lewis acid such as 48 % hydrobromic acid, 85 % phosphoric acid, polyphosphoric acid, aluminum chloride and aluminum bromide.

When 48 % hydrobromic acid, 85 % phosphoric acid and polyphosphoric acid are used as a cyclizing agent in this reaction, a range of reaction temperature is normally from 100° to 250°C., preferably from 120° to 220°C. Further, using aluminum chloride and aluminum bromide as a cyclizing reagent, this reaction is carried out in the presence of a suitable solvent such as carbon disulfide, carbon tetrachloride, dichloromethane, dichloroethane and nitrobenzene. A range of temperature in this reaction is normally from 20° to 100°C.

When 2-substituted 6,7-benzomorphan derivative of the formula [I] (R is an alkanoyloxy group) is desired, the purpose is easily performed, by acylating the compound of the formula [I] (R is a hydroxyl group) with an acid anhydride or an acyl halide.

When there is an alkyl group in the 9-position ($R_2$ is a $C_1$–$C_3$ alkyl group), the compounds of this invention have two stereoisomers, cis-compound ($R_2$ is the α-position) and trans-compound ($R_2$ is the β-position). In addition, each of these isomers has asymmetric carbon atoms, and accordingly there are obtained four optical active isomers ((+)-cis, (−)-cis, (+)-trans, (−)-trans) by a conventional optical resolution method.

The 2-substituted 6,7-benzomorphan derivative obtained according to the above-mentioned process may also be isolated in the form of an acid addition salt by treatment with an organic or inorganic acid such as formic acid, acetic acid, butyric acid, malic acid, fumaric acid, succinic acid, glutamic acid, tartaric acid, oxalic acid, citric acid, lactic acid, glycolic acid, gluconic acid, glucuronic acid, saccharic acid, ascorbic acid, benzoic acid, phthalic acid, salicylic acid, glyceric acid, anthranilic acid, cholic acid, picolinic acid, picric acid, tropic acid, indoleacetic acid, barbituric acid, sulfamic acid, methanesulfonic acid, ethanesulfonic acid, benzenesulfonic acid, p-toluenesulfonic acid, hydrochloric acid, hydrobromic acid, hydroiodic acid, sulfuric acid, phosphoric acid or the like.

According to the process of the present invention, there are produced such 2-substituted 6,7-benzomorphan derivatives and acid addition salts thereof as shown below.

2′-Hydroxy-2-(3-p-fluorobenzoyl-1-propyl)-5,9-dimethyl-6,7-benzomorphan

2′-Hydroxy-2-(3-p-fluorobenzoyl-1-propyl)-5,9-diethyl-6,7-benzomorphan

2′-Hydroxy-2-(3-m-fluorobenzoyl-1-propyl)-5,9-dimethyl- 6,7-benzomorphan

2′-Hydroxy-2-(4p-fluorobenzoyl-1-butyl)-5,9-dimethyl-6,7-benzomorphan

2′-Hydroxy-2-(3-p-trifluoromethylbenzoyl)-1-propyl)-5,9-dimethyl-6,7-benzomorphan 2′-Hydroxy-2-(3-m-trifluoromethylbenzoyl-1-propyl)-5-methyl-9-ethyl-6,7-benzomorphan 2′-Hydroxy-2-(3-p-chlorobenzoyl-1-propyl)-5,9-dimethyl-6,7-benzomorphan 2-(3-p-Fluorobenzoyl-1-propyl)-5,9-dimethyl-6,7-benzomorphan 2′-Hydroxy-2-(3-p-methylbenzoyl-1-propyl)-5,9-dimethyl-6,7-benzomorphan 2′-Hydroxy-2-[3-(2,5-dimethylbenzoyl)-1-propyl]-5-methyl-9-ethyl-6,7-benzomorphan 2'-Hydroxy-2-(3-benzoyl-1-propyl)-5,9-dimethyl-6,7-benzomorphan 2'-Hydroxy-2-(3-p-methylthiobenzoyl-1-propyl)-5,9-dimethyl-6,7 -benzomorphan 2'-Hydroxy-2-[3-(3-fluoro-4-methyl) benzoyl-1-propyl]-5,9-dimethyl-6,7-benzomorphan 2'-Methoxy-2-(3-p-fluorobenzoyl-1-propyl)-5,9-dimethyl-6,7-benzomorphan 2'-Hydroxy-2-(3-benzoyl-1-propyl)-5-methyl-9-ethyl-6,7-benzomorphan 2-(3-Benzoyl-1-propyl)-5,9-dimethyl-6,7-benzomorphan 2-(4-p-Fluorobenzoyl-1-butyl)-5,9-diethyl-6,7-benzomorphan 2'-Methoxy-2-(3-p-methoxybenzoyl-1-propyl)-5-methyl-9-ethyl-6,7-benzomorphan 2'-Hydroxy-2-(3-p-methylbenzoyl-1-propyl)-5-propyl-9-methyl-6,7-benzomorphan 2'-Methoxy-2-[3-(3-fluoro-4-methyl) benzoyl-1-propyl]-5,9-dimethyl-6,7-benzomorphan 2-[3-(2,5-Dimethylbenzoyl)-1-propyl]-5-methyl-9-ethyl-6,7-benzomorphan 2'-Methoxy-2-(3-p-methylthiobenzoyl-1-propyl)-5,9-dimethyl-6,7-benzomorphan 2-(3-Benzoyl-1-propyl)-5-methyl-9-ethyl-6,7-benzomorphan 2'-Hydroxy-2-(4-p-chlorobenzoyl-1-butyl)-5-propyl-9-6,7-benzomorphan 2'-Methoxy-2-(3-p-chlorobenzoyl-1-propyl)-5,9-dimethyl-6,7-benzomorphan 2-(3-p-Trifluoromethylbenzoyl-1-propyl)-5-methyl-9-ethyl-6,7-benzomorphan 2'-Hydroxy-2-(4-p-trifluoromethylbenzoyl-1-butyl)-5,9-dimethyl-6,7-benzomorphan 2'-Hydroxy-2-(3-p-fluorobenzoyl-1-propyl)-6,7-benzomorphan 2'-Methoxy-2-(3-p-fluorobenzoyl-1-propyl)-6,7-benzomorphan 2-(3-p-Fluorobenzoyl-1-propyl)-6,7-benzo-morphan 2'-Hydroxy-2-(β-p-fluorobenzoylethyl-6,7-benzomorphan 2'-Hydroxy-2-(3-p-fluorobenzoyl-1-propyl)-5-methyl-6,7-benzomorphan 2'-Hydroxy-2-(3-p-fluorobenzoyl-1-propyl)-5-phenyl-6,7-benzomorphan 2'-Hydroxy-2-(4-p-fluorobenzoyl-1-butyl)-6,7-benzomorphan 2'-Hydroxy-2-(β-p-fluorobenzoylethyl)-5-methyl-6,7-benzomorphan 2'-Hydroxy-2-(β-p-fluorobenzoylethyl)-5,9-dimethyl-6,7-benzomorphan 2'-Hydroxy-2-(β-p-fluorobenzoylethyl)-5-phenyl-6,7-benzomorphan 2'-Hydroxy-2-(3-m-fluorobenzoyl-1-propyl)-6,7-benzomorphan 2'-Hydroxy-2-[3-(2,5-dimethylbenzoyl)-1-propyl]-5-phenyl-6,7-benzomorphan 2-(3-p-Fluorobenzoyl-1-propyl)-5-methyl-6,7-benzomorphan 2-(3-p-Fluorobenzoyl-1-propyl)-5-phenyl-6,7-benzomorphan 2'-Hydroxy-2-(3-benzoyl-1-propyl)-5-methyl-6,7-benzomorphan 2'-Hydroxy-2-(3-benzoyl-1-propyl)-6,7-benzomorphan 2-(3-p-Methoxybenzoyl-1-propyl)-6,7-benzomorphan 2-(3-Benzoyl-1-propyl)-6,7-benzomorphan 2-(3-p-Methoxybenzoyl-1-propyl)-5,9-dimethyl-6,7-benzomorphan 2-(3-p-Methoxybenzoyl-1-propyl)-5-methyl-6,7-benzomorphan 2-(3-Benzoyl-1-propyl)-5-methyl-6,7-benzomorphan 2-(3-p-Methoxybenzoyl-1-propyl)-9-methyl-6,7-benzomorphan 2-(3-p-Fluorobenzoyl-1-propyl)-9methyl-6,7-benzomorphan 2'-Acetoxy-2-(3-fluorobenzoyl-1-propyl)-5,9-dimethyl-6,7-benzomorphan 2'-Hydroxy-2-(3-p-fluorobenzoyl-1-propyl)-9-methyl-6,7-benzomorphan 2'-Hydroxy-2-(β-p-fluorobenzoylethyl)-9-methyl-6,7-benzomorphan 2-(β-p-Fluorobenzoylethyl)-6,7-benzomorphan 2-(β-p-Fluorobenzoylethyl)-5-methyl-6,7-benzomorphan 2-(β-p-Fluorobenzoylethyl)-5,9-dimethyl-6,7-benzomorphan 2-(β-p-Methoxybenzoylethyl)-6,7-benzomorphan 2'-Hydroxy-2-(3-benzoyl-1-propyl)-9-methyl-6,7-benzomorphan 2-(3-Benzoyl-1-propyl)-9-methyl-6,7-benzomorphan 2'-Methoxy-2-(β-p-methoxybenzoylethyl)-6,7-benzomorphan 2'-Hydroxy-2-(β-benzoylethyl)-5,9-dimethyl-6,7-benzomorphan 2'-Hydroxy-2-(β-benzoylethyl)-5-methyl-6,7-benzomorphan 2'-Hydroxy-2-(β-benzoylethyl)-9-methyl-6,7-benzomorphan 2'-Hydroxy-2-(β-benzoylethyl)-6,7-benzomorphan In the next place, the process for preparing the 1-substituted 1,2,5,6-tetrahydropyridine compounds of the formula [II] is explained below.

The compounds described above are prepared from appropriate pyridine derivatives as shown in the aforesaid reaction scheme.

The procedure comprises the steps of subjecting the pyridine derivatives of the formula [VI] to quaternization with alkyl halide derivatives of the formula [VII] to give pyridinium derivatives of the formula [IV], reacting said pyridine derivative with a Grignard reagent of the formula [V], and then reducing the resulting 1-substituted 1,2-dihydropyridine derivatives of the formula [III].

According to the above process, the pyridine derivatives of the formula [VI] can be converted into the corresponding pyridinium derivatives of the formula [IV]

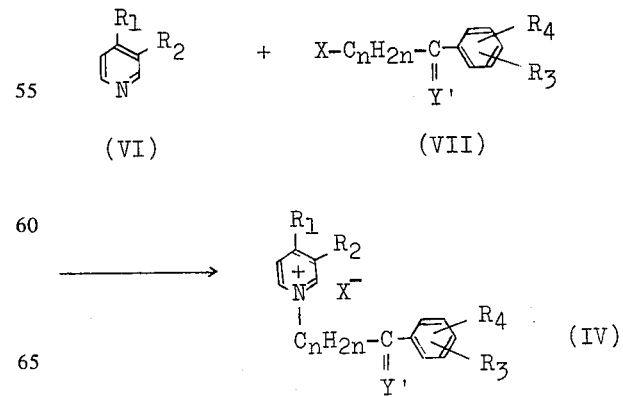

In practicing the above process, the pyridine derivative of the formula [VI] is quarternarized by the alkyl halide derivative of the formula [VII] in a suitable organic solvent to form the pyridinium derivaive of the formula [IV]. Preferable solvents include, for example, benzene, toluene, xylene, ether, tetrahydrofuran, dioxane, acetone, ethyl acetate, n-hexane, cyclohexane, chloroform, dichloromethane, methyl alcohol, ethyl alcohol and isopropanol alcohol.

A range of temperature in this reaction is normally from 30° to 200°C., preferably from 50° to 150°C. Preferably, this reaction is carried out in a sealed reaction vessel.

According to the above process, the following pyridinium derivatives are produced:

1-(4'-p-Fluorophenyl-4',4'-ethylenedioxy-1'-butyl)-3,4-dimethylpyridinium chloride
1-(4'-p-Methoxyphenyl-4',4'-ethylenedioxy-1'-butyl)-3,4-dimethylpyridinium chloride
1-(4'-Phenyl-4',4'-ethylenedioxy-1'-butyl)-3,4-dimethylpyridinium chloride
1-(4'-p-Fluorophenyl-4',4'-ethylenedioxy-1'-butyl)-4-methylpyridinium bromide
1-(4'-Phenyl-4',4'-ethylenedioxy-1'-butyl)-4-methylpyridinium chloride
1-(4'-p-Methoxyphenyl-4',4'-ethylenedioxy-1'-butyl)-4-methylpyridinium chloride
1-(4'-p-Fluorophenyl-4',4'-ethylenedioxy-1'-butyl)-pyridinium chloride
1-(4'-p-Methoxyphenyl-4',4'-ethylenedioxy-1'-butyl)-pyridinium chloride
1-(4',4'-ethylenedioxy-1'-butyl)-pyridinium chloride
1-(5'-p-Fluorophenyl-5',5'-ethylenedioxy-1'-pentyl)-3-ethyl-4-methylpyridinium chloride
1-(4'-p-Fluorophenyl-4',4'-ethylenedioxy-1'-butyl)-4-phenylpyridinium chloride
1-(3'-p-Fluorophenyl-3',3'-ethylenedioxy-1'-propyl)-3,4-dimethylpyridinium chloride
1-(3'-p-Methoxyphenyl-3',3'-ethylenedioxy-1'-propyl)-4-methylpyridinium chloride
1-(3'-p-Fluorophenyl-3',3'-ethylenedioxy-1'-propyl)-4-methylpyridinium chloride
1-(3'-p-Fluorophenyl-3',3'-ethylenedioxy-1'-propyl)-pyridinium chloride
1-(3'-Phenyl-3',3'-ethylenedioxy-1'-propyl)-4-phenylpyridinium chloride
1-[3'-(3,4-Dimethoxyphenyl)-3',3'-ethylene-dioxy-1'-propyl]-3,4-dimethylpyridinium chloride
1-(4'-p-Methylphenyl-4',4'-ethylenedioxy-1'-butyl)-3,4-dimethylpyridinium chloride
1-[4'-(3-Fluoro-4-methylphenyl)-4',4'-ethylenedioxy-1'-butyl]-3,4-dimethylpyridinium chloride
1-(4'-p-Trifluoromethylphenyl-4',4'-ethylene-dioxy-1'-butyl)-4-methylpyridinium chloride The thus obtained pyridinium derivatives of the formula [IV] are reacted with the Grignard reagent of the formula [V], whereby the novel 1-substituted 1,2-dihydropyridine derivatives of the formula [III] can be readily obtained.

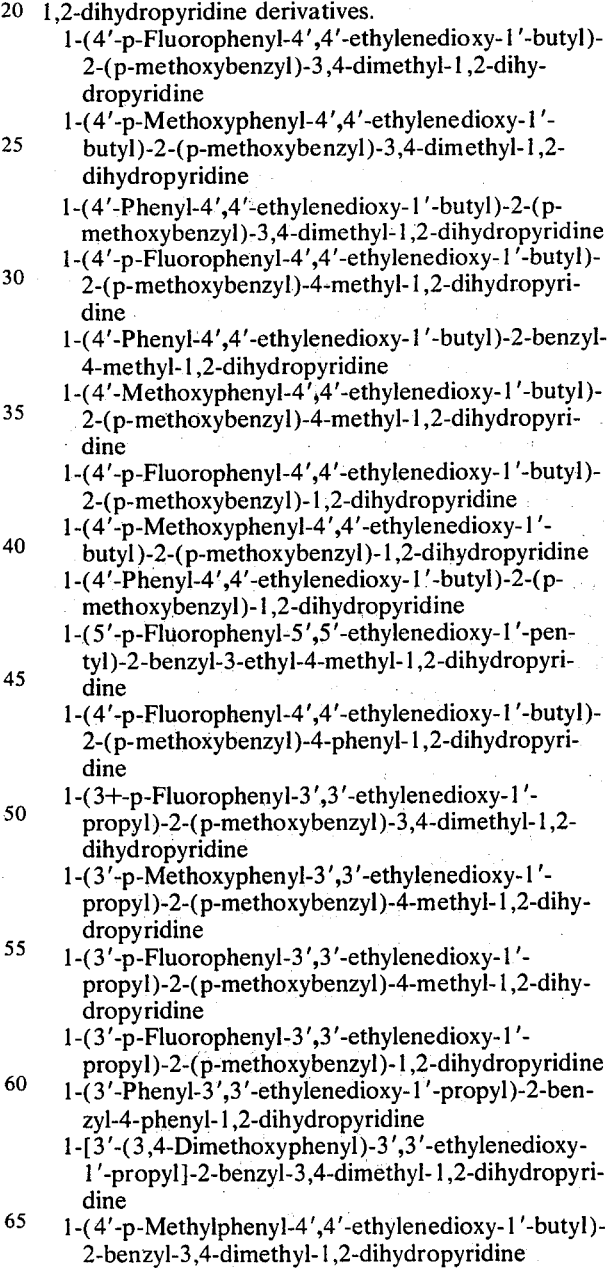

The above-mentioned process is carried out in a suitable anhydrous solvent, for example, anhydrous ether such as anhydrous ethyl ether and anhydrous tetrahydrofuran. The Grignard reagent of the formula [V] is easily obtained by reacting magnesium metal with a benzyl halide derivative in ether.

In accordance with the above process, there are obtained, for example, the following new 1-substituted 1,2-dihydropyridine derivatives.

1-(4'-p-Fluorophenyl-4',4'-ethylenedioxy-1'-butyl)-2-(p-methoxybenzyl)-3,4-dimethyl-1,2-dihydropyridine
1-(4'-p-Methoxyphenyl-4',4'-ethylenedioxy-1'-butyl)-2-(p-methoxybenzyl)-3,4-dimethyl-1,2-dihydropyridine
1-(4'-Phenyl-4',4'-ethylenedioxy-1'-butyl)-2-(p-methoxybenzyl)-3,4-dimethyl-1,2-dihydropyridine
1-(4'-p-Fluorophenyl-4',4'-ethylenedioxy-1'-butyl)-2-(p-methoxybenzyl)-4-methyl-1,2-dihydropyridine
1-(4'-Phenyl-4',4'-ethylenedioxy-1'-butyl)-2-benzyl-4-methyl-1,2-dihydropyridine
1-(4'-Methoxyphenyl-4',4'-ethylenedioxy-1'-butyl)-2-(p-methoxybenzyl)-4-methyl-1,2-dihydropyridine
1-(4'-p-Fluorophenyl-4',4'-ethylenedioxy-1'-butyl)-2-(p-methoxybenzyl)-1,2-dihydropyridine
1-(4'-p-Methoxyphenyl-4',4'-ethylenedioxy-1'-butyl)-2-(p-methoxybenzyl)-1,2-dihydropyridine
1-(4'-Phenyl-4',4'-ethylenedioxy-1'-butyl)-2-(p-methoxybenzyl)-1,2-dihydropyridine
1-(5'-p-Fluorophenyl-5',5'-ethylenedioxy-1'-pentyl)-2-benzyl-3-ethyl-4-methyl-1,2-dihydropyridine
1-(4'-p-Fluorophenyl-4',4'-ethylenedioxy-1'-butyl)-2-(p-methoxybenzyl)-4-phenyl-1,2-dihydropyridine
1-(3+-p-Fluorophenyl-3',3'-ethylenedioxy-1'-propyl)-2-(p-methoxybenzyl)-3,4-dimethyl-1,2-dihydropyridine
1-(3'-p-Methoxyphenyl-3',3'-ethylenedioxy-1'-propyl)-2-(p-methoxybenzyl)-4-methyl-1,2-dihydropyridine
1-(3'-p-Fluorophenyl-3',3'-ethylenedioxy-1'-propyl)-2-(p-methoxybenzyl)-4-methyl-1,2-dihydropyridine
1-(3'-p-Fluorophenyl-3',3'-ethylenedioxy-1'-propyl)-2-(p-methoxybenzyl)-1,2-dihydropyridine
1-(3'-Phenyl-3',3'-ethylenedioxy-1'-propyl)-2-benzyl-4-phenyl-1,2-dihydropyridine
1-[3'-(3,4-Dimethoxyphenyl)-3',3'-ethylenedioxy-1'-propyl]-2-benzyl-3,4-dimethyl-1,2-dihydropyridine
1-(4'-p-Methylphenyl-4',4'-ethylenedioxy-1'-butyl)-2-benzyl-3,4-dimethyl-1,2-dihydropyridine

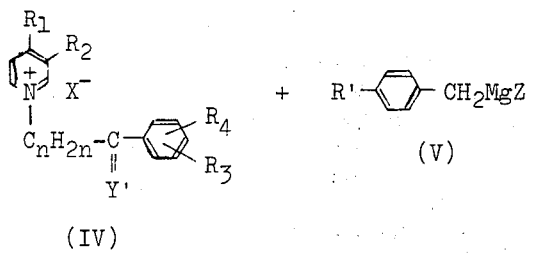

1-[4'-(3-Fluoro-4-methylphenyl)-4',4'-ethylene-
dioxy-1'-butyl]-2-(p-methoxybenzyl)-3,4-dimeth-
yl-1,2-dihydropyridine 1-(4'-p-Trifluoromethylphenyl-4',4'-ethylenedioxy-
1'-butyl)-2-(p-methoxybenzyl)-4-methyl-1,2-dihy-
dropyridine When the thus obtained 1-substituted 1,2-dihydropyridine derivatives of the formula [III] are reduced, the 1-substituted 1,2,5,6-tetrahydropyridine derivatives represented by the formula [II] can be easily produced.

For the production of the compounds represented by the formula [II], the 1-substituted 1,2-dihydropyridine derivatives of the formula [III] are ordinarily subjected to a process for the reduction of dihydropyridine to tetrahydropyridine. That is, the reduction of the said dihydropyridine derivatives is carried out according to, for example, reduction using boron hydride complexes which include sodium borohydride and potassium borohydride or catalytic reduction using palladium-barium sulfate catalysts. Particularly, the reduction using a boron hydride complex in neutral or alkaline alcohol solution with heating, and the catalytic reduction using palladium-barium sulfate in acidic solution are preferable.

After reduction, acid solution such as hydrochloric acid solution is used for purification or separation of the obtained 1-substituted 1,2,5,6-tetrahydropyridine derivative of the formula [II], in which some of Y=ethylenedioxy group of compound [II] is hydrolyzed to Y=oxygen atom by such treatment.

According to the above process, it is possible to prepare, for example, the following N-substituted tetrahydropyridine derivatives:

1-(4'-p-Fluorophenyl-4',4'-ethylenedioxy-1'-butyl)-
2-(p-methoxybenzyl)-3,4-dimethyl-1,2,5,6-tet-
rahydropyridine 1-(4'-p-Methoxyphenyl-4',4'-ethylenedioxy-1'-
butyl)-2-(p-methoxybenzyl)-3,4-dimethyl-1,2,5,6-
tetrahydropyridine 1-(4'-Phenyl-4',4'-ethylenedioxy-1'-butyl)-2-(p-
methoxybenzyl)-3,4-dimethyl-1,2,5,6-tetrahy-
dropyridine 1-(4'-p-Fluorophenyl-4',4'-ethylenedioxy-1'-butyl)-
2-(p-methoxybenzyl)-4-methyl-1,2,5,6-tetrahy-
dropyridine 1-(4'-Phenyl-4',4'-ethylenedioxy-1'-butyl)-2-benzyl-
4-methyl-1,2,5,6-tetrahydropyridine 1-(4'-p-Methoxyphenyl-4',4'-ethylenedioxy-1'-
butyl)-2-(p-methoxybenzyl)-4-methyl-1,2,5,6-tet-
rahydropyridine 1-(4'-p-Fluorophenyl-4',4'-ethylenedioxy-1'-butyl)-
2-(p-methoxybenzyl)-1,2,5,6-tetrahydropyridine 1-(4'-p-Methoxyphenyl-4',4'-ethylenedioxy-1'-
butyl)-2-(p-methoxybenzyl)-1,2,5,6-tetrahy-
dropyridine 1-(4'-Phenyl-4',4'-ethylenedioxy-1'-butyl)-2-(p-
methoxybenzyl)-1,2,5,6-tetrahydropyridine 1-(5'-p-Fluorophenyl-5',5'-ethylenedioxy-1'-pen-
tyl)-2-benzyl-3-ethyl-4-methyl-1,2,5,6-tetrahy-
dropyridine 1-(4'-p-Fluorophenyl-4',4'-ethylenedioxy-1'-butyl)-
2-(p-methoxybenzyl)-4-phenyl-1,2,5,6-tetrahy-
dropyridine 1-(3'-p-Fluorophenyl-3',3'-ethylenedioxy-1'-
propyl)-2-(p-methoxybenzyl)-3,4-dimethyl-
1,2,5,6-tetrahydropyridine 1-(3'-p-Methoxyphenyl-3',3'-ethylenedioxy-1'-
propyl)-2-(p-methoxybenzyl)-4-methyl-1,2,5,6-
tetrahydropyridine 1-(3'-p-Fluorophenyl-3',3'-ethylenedioxy-1'-
propyl)-2-(p-methoxybenzyl)-4-methyl-1,2,5,6-
tetrahydropyridine 1-(3'-p-Fluorophenyl-3',3'-ethylenedioxy-1'-
propyl)-2-(p-methoxybenzyl)-1,2,5,6-tetrahy-
dropyridine 1-(3'-Phenyl-3',3'-ethylenedioxy-1'-propyl)-2-ben-
zyl-4-phenyl-1,2,5,6-tetrahydropyridine 1-[3'-(3,4-Dimethoxyphenyl)-3',3'-ethylenedioxy-
1'-propyl]-2-benzyl-3,4-dimethyl-1,2,5,6-tetrahy-
dropyridine 1-(4'-p-Methylphenyl-4',4'-ethylenedioxy-1'-butyl)-
2-benzyl-3,4-dimethyl-1,2,5,6-tetrahydropyridine 1-[4'-(3'-Fluoro-4-methylphenyl)-4',4'-ethylene-
dioxy-1'-butyl]-2-(p-methoxybenzyl)-3,4-dimeth-
yl-1,2,5,6-tetrahydropyridine 1-(4'-p-Trifluoromethylphenyl-4',4'-ethylenedioxy-
1'-butyl)-2-(p-methoxybenzyl)-4-methyl-1,2,5,6-
tetrahydropyridine 1-(3-p-Fluorobenzoyl-1-propyl)-2-(p-methoxyben-
zyl)-3,4-dimethyl-1,2,5,6-tetrahydropyridine 1-(3-p-Fluorobenzoyl-1-propyl)-2-benzyl-4-methyl-
1,2,5,6-tetrahydropyridine 1-(2-Benzoylethyl)-2-(p-methoxybenzyl)-3,4-
dimethyl-1,2,5,6-tetrahydropyridine The above-mentioned novel compounds of the formula [II] can also form salts with organic and inorganic acids such as, hydrochloric, hydrobromic, sulfuric, nitric, phosphoric, maleic, fumaric, succinic, formic, tartaric, mandelic, lactic, oxalic or acetic acid.

The thus obtained tetrahydropyridine derivatives of the formula [II] or salts thereof are cyclized according to the procedures described above, whereby they can be readily converted to 2-substituted 6,7-benzomorphan derivatives of the formula [I] which are the desired products of the present process.

This invention is further disclosed in the following examples of preferred embodiments thereof, which are presented for purposes of illustration and are not intended to limit the scope of the invention.

EXAMPLE 1

To a mixture of 5.4 g of 3,4-lutidine, 25 ml of benzene and 5 ml of acetone is added 12.2 g of 4-(p-fluorophenyl)-4,4-ethylenedioxy-1-chlorobutane. Thereafter, stirring is continued at the boiling point of solvents mixture for 12 hours. After the reaction mixture is cooled, the crystals produced are collected by filtration, and recrystallized from acetone-methanol to give 1-(4'-p-fluorophenyl-4',4'-ethylenedioxy-1'-butyl)-3,4-dimethylpyridinium chloride, which has a melting point of 199° – 202°C.

IR$\nu_{max}^{paraffin}$: 1640, 1602, 1515, 1499, 1490, 1240, 1230, 1215, 1162, 1043, 865 cm$^{-1}$.

EXAMPLE 2

A mixture of 7 g of γ-picoline, 12.2 g of 4-(p-fluorophenyl)-4,4-ethylenedioxy-1-chlorobutane and 50 ml of isopropyl alcohol is stirred at 90° – 100°C for 7 hours in a 200 ml content autoclave, and then the mixture is concentrated to a red brown oily residue, which is crystallized with cooling. Thereafter, the resulting residue is washed with ether and the crystals are recrystallized from acetone-methanol (50 : 1) to give 1-(4'-p-fluorophenyl-4',4'-ethylenedioxy-1'-butyl)-4-methylpyridinium chloride, a melting point of 168° – 171°C.

According to the procedure of Example 2, there is obtained the following compounds:

1-(5'-p-Methoxyphenyl-5',5'-ethylenedioxy-1'-pentyl)-3,4-dimethylpyridinium chloride, melting point: 166° – 170°C.

1-(4'-p-Fluorophenyl-4',4'-ethylenedioxy-1'-butyl)-pyridinium chloride, which is very hygroscopic crystals having a melting point of 63° – 73°C.
IR$\nu_{max.}^{paraffin}$: 3400, 1630, 1618, 1600, 1510, 1502, 1495, 1227, 1218, 1182, 950, 838, 790, 690 cm$^{-1}$.

1-(4'-p-Methylphenyl-4',4'-ethylenedioxy-1'-butyl)-3-methylpyridinium chloride, which is a viscous oil.
IR$\nu_{max.}^{liq.}$: 3340, 1678, 1630, 1603, 1550, 1500, 1040, 940, 800 cm$^{-1}$.

EXAMPLE 3

To a suspension of magnesium turnings (1.74 g) in 50 ml of anhydrous ether is added dropwise 2.7 g of p-methoxybenzyl chloride in 30 ml of dry ether with vigorous stirring. Thereafter, stirring is continued for one hour at the boiling temperature. Fine magnesium powder is removed by filtration.

To a suspension of 4.2 g of 1-(4'-p-fluorophenyl-4',-4'-ethylenedioxy-1'-butyl)-3,4-dimethylpyridinium chloride in 20 ml of dry ether is added the resulting Grignard solution with vigorous stirring. The mixture is stirred at room temperature for one hour and then refluxed for 4 hours. After cooling, the resulting ether solution is poured into a mixture of 100 ml of ice-water, 10 g of ammonium chloride and 5 ml of aqueous ammonia with stirring. The ethereal layer is washed with an aqueous solution saturated with sodium chloride, dried over anhydrous magnesium sulfate and then concentrated to give 1-(4'-p-fluorophenyl-4',4'-ethylenedioxy-1'-butyl)-2-(p-methoxybenzyl)-3,4-dimethyl-1,2-dihydropyridine which is a yellow oily substance.
IR$\nu_{max.}^{liq.}$: 1650 (weak), 1610, 1580, 1510, 1440 1300, 1248, 1175, 1030, 830 cm$^{-1}$.

According to the similar procedure of Example 3, there are obtained the following compounds as yellow oily substances.

1-(4'-p-Fluorophenyl-4',4'-ethylenedioxy-1'-butyl)-2-(p-methoxybenzyl)-4-methyl-1,2-dihydropyridine
IR$\nu_{max.}^{liq.}$: 1640 (weak), 1610, 1585, 1510, 1245, 1176, 1033, 832, 820 cm$^{-1}$.

1-(5'-p-Methoxyphenyl-5',5'-ethylenedioxy-1'-pentyl)-2-(p-methoxybenzyl)-3,4-dimethyl-1,2-dihydropyridine
IR$\nu_{max.}^{liq.}$: 1640 (weak), 1608, 1580, 1505, 1240, 1175, 1029, 820 cm$^{1}$.

EXAMPLE 4

To a mixture of 4.2 g of 1-(4'-p-fluorophenyl-4',4'-ethylenedioxy-1'-butyl)-2-(p-methoxybenzyl)3,4-dimethyl-1,2-dihydropyridine, 17 ml of methanol and 10 ml of 1N-sodium hydroxide is added 0.35 g of sodium borohydride. After stirring at 50° – 65°C for 2 hours, the mixture is diluted with 30 ml of ice-water and extracted with 90 ml of ether. The ether layer is then extracted with 10 % hydrochloric acid, but an oily substance which is not soluble in ether and 10 %-hydrochloric acid is produced. This oily substance is combined to the 10%-hydrochloric acid layer. The mixture is then made alkaline with sodium carbonate. The alkaline solution is extracted with chloroform. This chloroform layer is concentrated to a yellow oily residue.

The residue is distilled under reduced pressure to give 1-(3'-p-fluorobenzoyl-1'-propyl)-2-(p-methoxybenzyl)-3,4-dimethyl-1,2,5,6-tetrahydropyridine, b.p.: 196° – 215°C/0.3 mmHg.
IR$\nu_{max.}^{liq.}$: 1690, 1610, 1600, 1510cm$^{-1}$ NMR (CDCl$_3$).

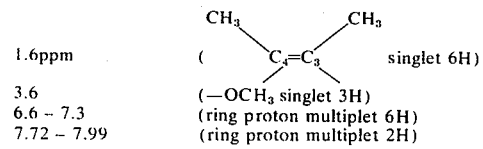

| 1.6ppm | | singlet 6H |
| 3.6 | | (—OCH$_3$ singlet 3H) |
| 6.6 – 7.3 | | (ring proton multiplet 6H) |
| 7.72 – 7.99 | | (ring proton multiplet 2H) |

According to the procedure of Example 4, there are obtained the following compounds.

1-(3'-p-Fluorobenzoyl-1'-propyl)-2-(p-methoxybenzoyl)-4-methyl-1,2,5,6-tetrahydropyridine
IR$\nu_{max.}^{liq.}$: 1680, 1610, 1600, 1512, 1247, 1178, 1158, 1037, 825 cm$^{-1}$.

1-(5'-p-Methoxyphenyl-5',5'-ethylenedioxy-1'-pentyl)-2-(p-methoxybenzyl)-3,4-dimethyl-1,2,5,6-tetrahydropyridine
IR$\nu_{max.}^{liq.}$: 1610, 1582, 1509, 1300, 1245, 1173, 1108, 1032, 830 cm$^{-1}$.
NMR (CDCl$_3$)

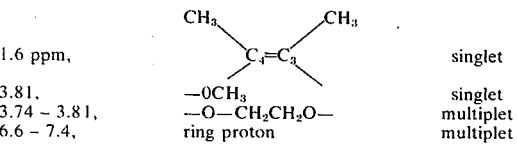

| 1.6 ppm, | | singlet |
| 3.81, | —OCH$_3$ | singlet |
| 3.74 – 3.81, | —O—CH$_2$CH$_2$O— | multiplet |
| 6.6 – 7.4, | ring proton | multiplet |

EXAMPLE 5

To a suspension of 2.2 g of 1-(3'-p-fluorobenzoyl-1'-propyl)-2-(p-methoxybenzyl)-3,4-dimethyl-1,2,5,6-tetrahydropyridine hydrochloride in 20 ml of carbon disulfide is added 4.0 g of aluminum bromide. The reaction mixture is stirred at 50°C for 4 hours, and concentrated to a residue. To this residue is added 25 ml of 48 % hydrobromic acid. The mixture is then refluxed for 2.5 hours. Thereafter, the mixture is poured into ice-water and the solution is made alkaline with aqueous ammonia. The alkaline solution is extracted with chloroform. The chloroform extract is washed with water, dried over anhydrous sodium sulfate and concentrated to a yellow oily residue.

To the oily residue is added a little amount of acetone, and then the crystals produced, recrystallized from ethyl acetate to give 2'-hydroxy-2-(3-p-fluorobenzoyl-1-propyl)-5,9-dimethyl-6,7-benzomorphan, m.p.: 166° – 169°C.

EXAMPLE 6

A mixture of 0.48 g of 1-(3'-p-fluorobenzoyl-1'-propyl)-2-(p-methoxybenzyl)-4-methyl-1,2,5,6-tetrahydropyridine and 40 ml of 48 % hydrobromic acid is stirred at 125° – 130°C for 16.5 hours in a stream of nitrogen.

The reaction mixture is poured into ice-water and made alkaline with aqueous ammonia. The solution is extracted with chloroform. The chloroform extract is washed with water, dried over anhydrous sodium sulfate and concentrated to a brown residue, which is chromatographed on a slica gel. The fraction which is eluted with acetone is crystallized, and then recrystallized from ethyl acetate to give 2'-hydroxy-2-(3-p-fluorobenzoyl-1-propyl)-5-methyl-6,7-benzomorphan, m.p.: 169.5° – 171.5°C.

EXAMPLE 7

To a mixture of phosphorus pentoxide (12.5 g) and 85 % phosphoric acid (16.5 g) is added 3 g of 1-(3'-p-fluorobenzoyl-1'-propyl)-2-benzyl-3,4-dimethyl-1,2,5,6-tetrahydropyridine. The mixture is stirred at 135° – 150°C for 20 hours in a stream of nitrogen. The mixture is poured into ice-water and the solution is then made alkaline with aqueous ammonia. The alkaline solution is extracted with ether. The ethereal extract is washed with an aqueous solution saturated with sodium chloride, dried over anhydrous sodium sulfate and concentrated to a brown oily substance.

The residue is distilled under reduced pressure to give 2-(3-p-fluorobenzoyl-1-propyl)-5,9-dimethyl-6,7-benzomorphan, b.p.: 140° – 150°C/0.5 mmHg. This 6,7-benzomorphan is dissolved in ether and gaseous hydrogen chloride is introduced to the solution. The ether is removed, and the residue is recrystallized from acetone-ether to give 2-(γ-p-fluorobenzoyl-n-propyl)-5,9-dimethyl-6,7-benzomorphan hydrochloride, m.p.: 164° – 166°C.

In a similar manner to that of Examples 5, 6 and 7, there are obtained the compounds as listed in Table 1.

TABLE 1

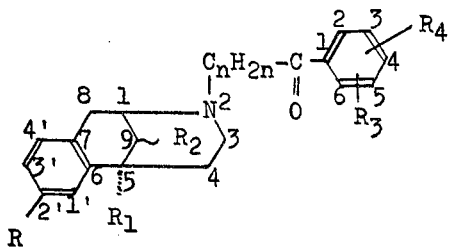

| Example No. | R | $R_1$ | $R_2$ | $R_3$ | $R_4$ | n | m.p. (°C) |
|---|---|---|---|---|---|---|---|
| 8 | OH | $CH_3$ | $C_2H_5$ | 4-F | H | 3 | 160 – 165 |
| 9 | OH | $CH_3$ | $CH_3$ | 4-Cl | H | 3 | 179 – 181 |
| 10 | OH | $CH_3$ | $CH_3$ | 4-$OCH_3$ | H | 3 | 148 – 152.8 |
| 11 | OH | $CH_3$ | $CH_3$ | 4-$CH_3$ | H | 3 | 157.5 – 164.5 |
| 12 | OH | $CH_3$ | $CH_3$ | 4-$CF_3$ | H | 3 | 116.5 – 120 |
| 13 | OH | $CH_3$ | $C_2H_5$ | 4-$OCH_3$ | H | 3 | 148.5 – 150 |
| 14 | OH | $CH_3$ | $CH_3$ | 4-F | H | 4 | 229 – 231 (Hydrochloride) |
| 15 | OH | $CH_3$ | $CH_3$ | 4-$OCH_3$ | H | 4 | 181 – 182 |
| 16 | OH | $CH_3$ | $CH_3$ | 2-$OCH_3$ | H | 3 | 132 – 137 |
| 17 | OH | $CH_3$ | $C_2H_5$ | 2-$CH_3$ | 5-$CH_3$ | 3 | 152 – 155 |
| 18 | OH | $CH_3$ | $CH_3$ | 3-$CF_3$ | H | 3 | 137 – 139 |
| 19 | OH | $CH_3$ | $C_2H_5$ | 2-$OCH_3$ | H | 3 | 148 – 151 |
| 20 | OH | $CH_3$ | $CH_3$ | 3-$OCH_3$ | 4-$OCH_3$ | 3 | 156 – 158 |
| 21 | OH | $CH_3$ | $CH_3$ | 3-F | 4-$CH_3$ | 3 | 131 – 134 |
| 22 | OH | $CH_3$ | $CH_3$ | 4-$SCH_3$ | H | 3 | 154 – 156 |
| 23 | OH | $CH_3$ | $CH_3$ | H | H | 3 | 172 – 174 |
| 24 | OH | $CH_3$ | $C_2H_5$ | H | H | 3 | 168 – 170 |
| 25 | OH | $CH_3$ | $CH_3$ | 4-F | H | 2 | 156.5 – 160 |
| 26 | OH | ⟨phenyl⟩ | H | 4-F | H | 3 | 170 – 173 |
| 27 | OH | H | H | 4-F | H | 3 | 165.5 – 169.5 |
| 28 | OH | $CH_3$ | $CH_3$ | 4-F | H | 3 | 214 – 217 (Hydrochloride) |
| 29 | OH | $CH_3$ | $CH_3$ | 4-$OCH_3$ | H | 4 | 128 – 130 |
| 30 | H | $CH_3$ | H | 4-F | H | 3 | 219 – 220 (Hydrochloride) |
| 31 | H | $CH_3$ | $CH_3(\beta)$ | 4-F | H | 3 | 209.5 – 210.5 (Hydrochloride) |
| 32 | $OCH_3$ | $CH_3$ | $CH_3$ | 4-F | H | 3 | 144 – 152 (Hydrochloride) |
| 33 | OH | $CH_3$ | $CH_3$ | 3-F | H | 3 | 167 – 170 |
| 34 | OH | $CH_3$ | $CH_3(\beta)$ | 4-F | H | 3 | 133.5 – 135 |
| 35 | H | H | H | 4-F | H | 3 | 209 – 211 (Hydrochloride) 211.5 – 213 |

TABLE 1 -continued

| Example No. | R | $R_1$ | $R_2$ | $R_3$ | $R_4$ | n | m.p. (°C) |
|---|---|---|---|---|---|---|---|
| 36 | H | H | H | 4-OCH$_3$ | H | 3 | 188 – 189.5 (Hydrochloride) |
| 37 | OCOCH$_3$ | CH$_3$ | CH$_3$ | 4-F | H | 3 | 218 – 221 (acetate) |
| 38 | H | CH$_3$ | H | H | H | 3 | 241 – 249 (Hydrochloride) |
| 39 | H |  | H | 4-F | H | 2 | 177 – 178 (Hydrochloride) |
| 40 | H | CH$_3$ | H | 4-F | H | 2 | (Hydrochloride) |
| 41 | OH |  | H | H | H | 3 | 175 – 181 |
| 42 | OH | CH$_3$ | CH$_3$ | H | H | 2 | 164 – 167 |
| 43 | H |  | H | 4-F | H | 3 | 248 – 250 (Hydrochloride) |

What is claimed is:

1. A process for preparing 2-substituted 6,7-benzomorphan derivatives, and salts thereof, represented by the general formula,

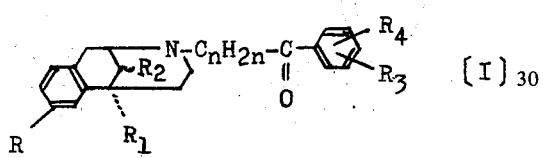

wherein R is a hydrogen atom, a hydroxyl group, a $C_1$–$C_3$ alkoxy group or an alkanoyloxy group; $R_1$ is a hydrogen atom, a $C_1$–$C_3$ alkyl group, a phenyl group, a halophenyl group, a $C_1$–$C_3$ alkylphenyl group, a $C_1$–$C_3$ alkoxyphenyl group, a hydroxyphenyl group, a trifluoromethylphenyl group, a nitrophenyl group, an aminophenyl group, a $C_1$–$C_3$ alkylthiophenyl group or an alkanoyloxyphenyl group; $R_2$ is a hydrogen atom or a $C_1$–$C_3$ alkyl group; $R_3$ is a hydrogen atom, a halogen atom, a $C_1$–$C_3$ alkyl group, a $C_1$–$C_3$ alkoxy group, a $C_1$–$C_3$ alkylthio group, a nitro group, a trifluoromethyl group, an amino group or a hydroxyl group; $R_4$ is a hydrogen atom, a $C_1$–$C_3$ alkoxy group, a halogen atom or a $C_1$–$C_3$ alkyl group; and n is an integer of 2 to 4, which process comprises cyclizing a 1-substituted 1,2,5,6-tetrahydropyridine derivative or a salt thereof, represented by the general formula,

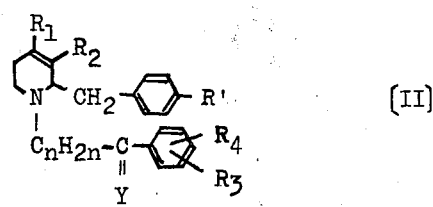

wherein $R_1$, $R_2$, $R_3$, $R_4$ and n are as defined above; Y is an oxygen atom or an ethylenedioxy group; and R' is a hydrogen atom or a $C_1$–$C_3$ alkoxy group.

2. A process according to claim 1, wherein the cyclizing agent is a Lewis acid selected from the group consisting of 48 % hydrobromic acid, 85 % phosphoric acid, polyphosphoric acid, aluminum chloride and aluminum bromide.

3. A process according to claim 1, wherein the reaction is carried out at a temperature within a range between 30°C and 250°C.

4. A process for preparing 2-substituted 6,7-benzomorphan derivatives, and salts thereof, represented by the general formula,

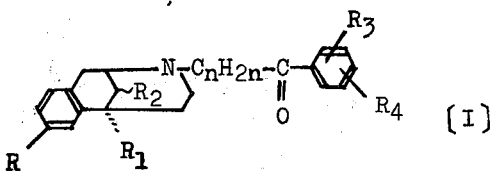

wherein R is a hydrogen atom, a hydroxyl group, a $C_1$–$C_3$ alkoxy group or an alkanoyloxy group; $R_1$ is a hydrogen atom, a $C_1$–$C_3$ alkyl group, a phenyl group, a halophenyl group, a $C_1$–$C_3$ alkylphenyl group, a $C_1$–$C_3$ alkoxyphenyl group, a hydroxyphenyl group, a trifluoromethylphenyl group, a nitrophenyl group, an aminophenyl group, a $C_1$–$C_3$ alkylthiophenyl group or an alkanoyloxyphenyl group; $R_2$ is a hydrogen atom or a $C_1$–$C_3$ alkyl group; $R_3$ is a hydrogen atom, a halogen atom, a $C_1$–$C_3$ alkyl group, a $C_1$–$C_3$ alkoxy group, a $C_1$–$C_3$ alkylthio group, a nitro group, a trifluoromethyl group, an amino group or a hydroxyl group; $R_4$ is a hydrogen atom, a $C_1$–$C_3$ alkoxy group, a halogen atom or a $C_1$–$C_3$ alkyl group; and n is an integer of 2 to 4, which process comprises reducing a 1-substituted 1,2-dihydropyridine derivative, represented by the general formula,

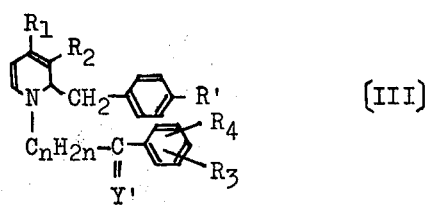

wherein $R_1$, $R_2$, $R_3$, $R_4$ and n are as defined above, R' is a hydrogen atom or a $C_1$–$C_3$ alkoxy group, and Y' is an ethylenedioxy group, then cyclizing with a Lewis acid selected from the group consisting of 48 % hydrobromic acid, 85 % phosphoric acid, polyphosphoric acid, aluminum chloride and aluminum bromide, the resulting 1-substituted 1,2,5,6-tetrahydropyridine derivative, or a salt thereof, represented by the general formula,

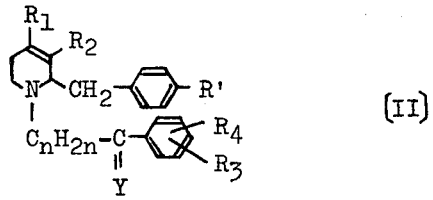

wherein R′, R₁, R₂, R₃, R₄ and n are as defined above and Y is an oxygen atom or an ethylenedioxy group.

5. A process according to claim 4, wherein the reduction of the 1-substituted 1,2-dihydropyridine derivative is carried out by contacting the 1-substituted 1,2-dihydropyridine derivative with a boron hydride complex or with hydrogen in the presence of a palladium-barium sulfate catalyst.

6. A process for preparing 2-substituted 6,7-benzomorphan derivatives, and salts thereof, represented by the general formula,

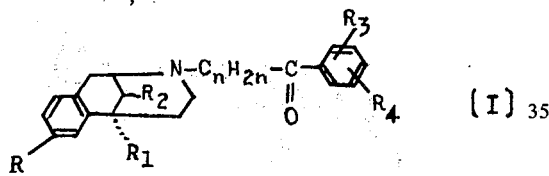

wherein R is a hydrogen atom, a hydroxyl group, a C₁-C₃ alkoxy group or an alkanoyloxy group; R₁ is a hydrogen atom, a C₁-C₃ alkyl group, a phenyl group, a halophenyl group, a C₁-C₃ alkylphenyl group, a C₁-C₃ alkoxyphenyl group, a hydroxyphenyl group, a trifluoromethylphenyl group, a nitrophenyl group, an aminophenyl group, a C₁-C₃ alkylthiophenyl group or an alkanoyloxyphenyl group; R₂ is a hydrogen atom or a C₁-C₃ alkyl group; R₃ is a hydrogen atom, a halogen atom, a C₁-C₃ alkyl group, a C₁-C₃ alkoxy group, a C₁-C₃ alkylthio group, a nitro group, a trifluoromethyl group, an amino group or a hydroxyl group; R₄ is a hydrogen atom, a C₁-C₃ alkoxy group, a halogen atom or a C₁-C₃ alkyl group; and n is an integer of 2 to 4, which process comprises reacting a pyridinium derivative represented by the general formula,

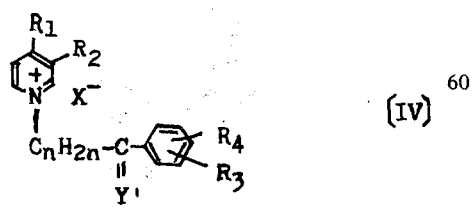

wherein X is a halogen atom, Y′ is an ethylenedioxy group and R₁, R₂, R₃, R₄ and n are as defined above, with a Grignard reagent represented by the general formula,

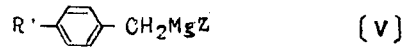

wherein Z is a halogen atom and R′ is a hydrogen atom or a C₁-C₃ alkoxy group; reducing the resulting 1-substituted 1,2-dihydropyridine derivative, represented by the general formula,

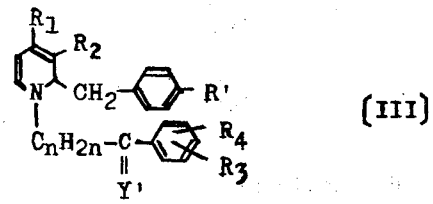

wherein R′, R₁, R₂, R₃, R₄, n and Y′ are as defined above; and then cyclizing with a Lewis acid selected from the group consisting of 48 % hydrobromic acid, 85 % phosphoric acid, polyphosphoric acid, aluminum chloride and aluminum bromide, the resulting 1-substituted 1,2,5,6-tetrahydropyridine derivative, or a salt thereof, represented by the general formula,

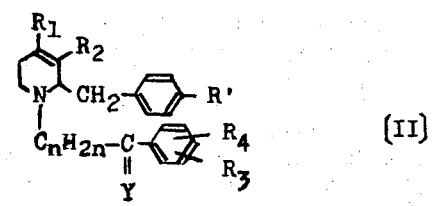

wherein R′, R₁, R₂, R₃, R₄ and n are as defined above and Y is an oxygen atom or an ethylenedioxy group.

7. A process for preparing 2-substituted 6,7-benzomorphan derivatives, and salts thereof, represented by the general formula,

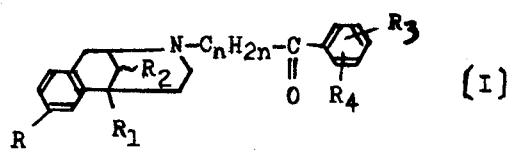

wherein R is a hydrogen atom, a hydroxyl group, or a C₁-C₃ alkoxy group; R₁ and R₂ are C₁-C₃ alkyl groups; R₃ and R₄ are hydrogen atoms, halogen atoms, C₁-C₃ alkyl groups, C₁-C₃ alkoxy groups, C₁-C₃ alkylthio groups, nitro groups, trifluoromethyl groups, amino groups, or hydroxyl groups; and n is 3 or 4, which comprises reacting a 1-substituted 1,2,5,6-tetrahydropyridine derivative, or a salt thereof, represented by the general formula,

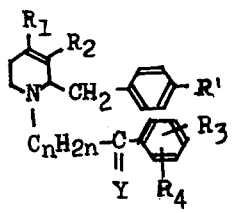

(II)

wherein $R_1$, $R_2$, $R_3$, $R_4$ and $n$ are the same as defined above; Y is an oxygen atom; R' is a hydrogen atom or a $C_1$–$C_3$ alkoxy group with a Lewis acid to effect ring closure.

8. A process for preparing 1-substituted 1,2,5,6-tetrahydropyridine derivatives represented by the general formula,

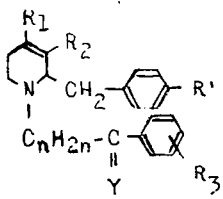

wherein R' is a hydrogen atom, or a $C_1$–$C_3$ alkoxy group; $R_1$ and $R_2$ are $C_1$–$C_3$ alkyl groups; $R_3$ is a hydrogen atom, a halogen atom, a trifluoromethyl group, a $C_1$–$C_3$ alkyl group, a $C_1$–$C_3$ alkoxy group, a hydroxyl group, or a nitro group; Y is an oxygen atom or an ethylenedioxy group; and $n$ is 3 or 4, which comprises reducing a 1-substituted 1,2-dehydropyridine derivative represented by the general formula,

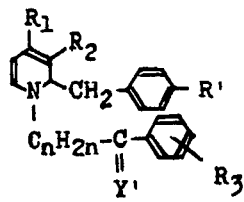

wherein R', $R_1$, $R_2$, $R_3$ and $n$ are the same as defined above, and Y' is an ethylenedioxy group.

9. A process for preparing 1-substituted 1,2-dihydropyridine derivatives represented by the formula,

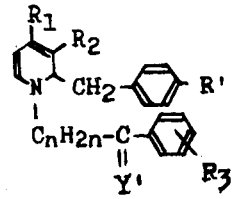

wherein R' is a hydrogen atom, or a $C_1$–$C_3$ alkoxy group; $R_1$ and $R_2$ are $C_1$–$C_3$ alkyl groups; $R_3$ is a hydrogen atom, a halogen atom, a trifluoromethyl group, a $C_1$–$C_3$ alkyl group, a $C_1$–$C_3$ alkoxy group, a hydroxyl group, or a nitro group; Y' is an ethylenedioxy group; and $n$ is 3 or 4, which comprises reacting a pyridinium derivative represented by the general formula,

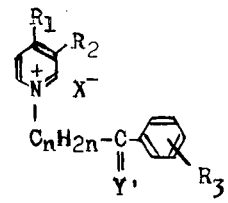

wherein X is a halogen atom; and $R_1$, $R_2$, $R_3$, Y' and $n$ are the same as defined above, with a Grignard reagent represented by the general formula,

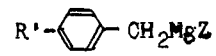

wherein Z is a halogen atom and R' is the same as defined above.

* * * * *